United States Patent
Sukegawa et al.

(10) Patent No.: US 10,157,802 B2
(45) Date of Patent: Dec. 18, 2018

(54) WORKPIECE EVALUATING METHOD

(71) Applicant: DISCO CORPORATION, Tokyo (JP)

(72) Inventors: Naoya Sukegawa, Tokyo (JP); Seiji Harada, Tokyo (JP)

(73) Assignee: Disco Corporation, Tokyo (JP)

( * ) Notice: Subject to any disclaimer, the term of this patent is extended or adjusted under 35 U.S.C. 154(b) by 0 days.

(21) Appl. No.: 15/461,784

(22) Filed: Mar. 17, 2017

(65) Prior Publication Data
US 2017/0278759 A1    Sep. 28, 2017

(30) Foreign Application Priority Data
Mar. 28, 2016  (JP) .................................. 2016-064621

(51) Int. Cl.
| | | |
|---|---|---|
| H01L 21/00 | (2006.01) | |
| H01L 21/66 | (2006.01) | |
| H01L 21/322 | (2006.01) | |
| G01N 22/02 | (2006.01) | |
| G01N 1/00 | (2006.01) | |

(52) U.S. Cl.
CPC ............. H01L 22/14 (2013.01); G01N 22/02 (2013.01); H01L 21/3221 (2013.01); *G01N 1/00* (2013.01); *G01N 2201/00* (2013.01); *H01L 2221/00* (2013.01)

(58) Field of Classification Search
CPC ....... H01L 21/00; H01L 2221/00; G01N 1/00; G01N 2201/00
See application file for complete search history.

(56) References Cited

U.S. PATENT DOCUMENTS

| | | | | |
|---|---|---|---|---|
| 9,702,913 B2* | 7/2017 | Ikeda | ........................ | H05H 1/46 |
| 2003/0003608 A1* | 1/2003 | Arikado | ................ | H01L 23/544 |
| | | | | 438/14 |
| 2003/0205664 A1* | 11/2003 | Abe | ...................... | B24B 37/013 |
| | | | | 250/214 R |
| 2005/0282359 A1* | 12/2005 | Nagai | .................. | B28D 5/0011 |
| | | | | 438/459 |
| 2015/0270105 A1* | 9/2015 | Kobayashi | ........ | H01J 37/32201 |
| | | | | 315/34 |
| 2016/0013023 A1* | 1/2016 | Taki | ........................ | C23C 16/26 |
| | | | | 427/575 |

FOREIGN PATENT DOCUMENTS

JP       2009-094326       4/2009

* cited by examiner

*Primary Examiner* — Jermele M Hollington
*Assistant Examiner* — Temilade Rhodes-Vivour
(74) *Attorney, Agent, or Firm* — Greer Burns & Crain Ltd.

(57) ABSTRACT

A workpiece evaluating method evaluates the gettering property of a device wafer having a plurality of devices formed on the front side of the wafer and having a gettering layer formed inside the wafer. The method includes the steps of applying excitation light for exciting a carrier to the wafer, applying microwaves to a light applied area where the excitation light is applied and also to an area other than the light applied area, measuring the intensity of the microwaves reflected from the light applied area and from the area other than the light applied area, subtracting the intensity of the microwaves reflected from the area other than the light applied area from the intensity of the microwaves reflected from the light applied area to thereby obtain a differential signal, and determining the gettering property of the gettering layer according to the intensity of the differential signal obtained above.

3 Claims, 12 Drawing Sheets

WORKPIECE EVALUATING METHOD

BACKGROUND OF THE INVENTION

Field of the Invention

The present invention relates to a workpiece evaluating method of evaluating the gettering property of a workpiece.

Description of the Related Art

In recent years, a wafer having a plurality of devices formed thereon (which will be hereinafter referred to as device wafer) has been thinned for the purposes of a size reduction of each device, for example. However, when the device wafer is polished to reduce the wafer thickness to 100 μm or less, there is a possibility of reduction in gettering property of suppressing the movement of metal elements harmful to the devices, causing a faulty operation of each device. To cope with this problem, a gettering layer for capturing the metal elements is formed inside the device wafer (see Japanese Patent Laid-open No. 2009-94326, for example). In this processing method, the device wafer is ground under predetermined conditions to thereby form the gettering layer including a predetermined strained layer as maintaining the die strength of the device wafer.

SUMMARY OF THE INVENTION

The gettering property of the device wafer processed by the processing method described in Japanese Patent Laid-open No. 2009-94326 may be evaluated by actually contaminating the device wafer with metal elements. However, this method has a problem such that good device chips (non-defective products) cannot be obtained. That is, since this evaluating method includes the step of actually contaminating the device wafer with metal elements, a device wafer that may become a product cannot be evaluated.

It is therefore an object of the present invention to provide a workpiece evaluating method which can evaluate the gettering property of a workpiece that may become a product.

In accordance with an aspect of the present invention, there is provided a workpiece evaluating method for evaluating the gettering property of a workpiece having a plurality of devices formed on the front side of the workpiece and having a gettering layer formed inside the workpiece, the workpiece evaluating method including an excitation light applying step of applying excitation light for exciting a carrier to the workpiece; a microwave applying step of applying microwaves to a light applied area where the excitation light is applied and also to an area other than the light applied area on the workpiece, after performing the excitation light applying step; a measuring step of measuring the intensity of the microwaves reflected from the light applied area and from the area other than the light applied area after performing the microwave applying step, and next subtracting the intensity of the microwaves reflected from the area other than the light applied area from the intensity of the microwaves reflected from the light applied area to thereby obtain a differential signal; and a gettering property determining step of determining the gettering property of the gettering layer according to the intensity of the differential signal obtained in the measuring step.

Preferably, the frequency of the microwaves is 26 GHz.

Preferably, the wavelength of the excitation light is 349 nm.

According to the present invention, it is possible to evaluate the gettering property of the workpiece that can become a product.

The above and other objects, features and advantages of the present invention and the manner of realizing them will become more apparent, and the invention itself will best be understood from a study of the following description and appended claims with reference to the attached drawings showing some preferred embodiments of the invention.

DETAILED DESCRIPTION OF THE PREFERRED EMBODIMENTS

Preferred embodiments of the present invention will now be described in detail with reference to the drawings. The present invention is not limited to these preferred embodiments. Further, the components used in these preferred embodiments may include those that can be easily assumed by persons skilled in the art or substantially the same elements as those known in the art. Further, the configurations described below may be suitably combined. Further, the configurations may be variously omitted, replaced, or changed without departing from the scope of the present invention.

First Preferred Embodiment

Figure 1:
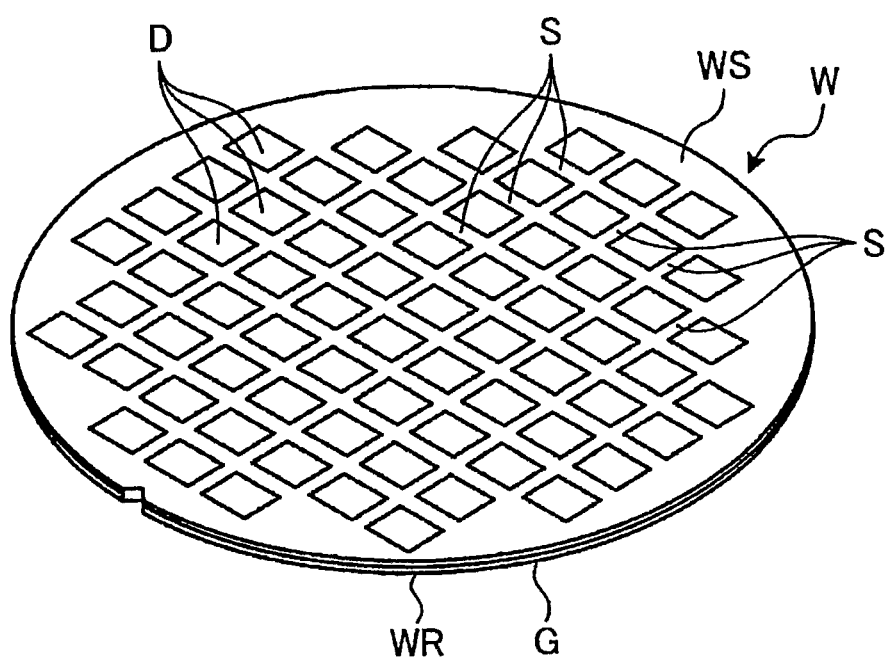
FIG. 1 is a perspective view showing a device wafer as a target to be evaluated in a workpiece evaluating method according to a first preferred embodiment of the present invention.
Figure 2:
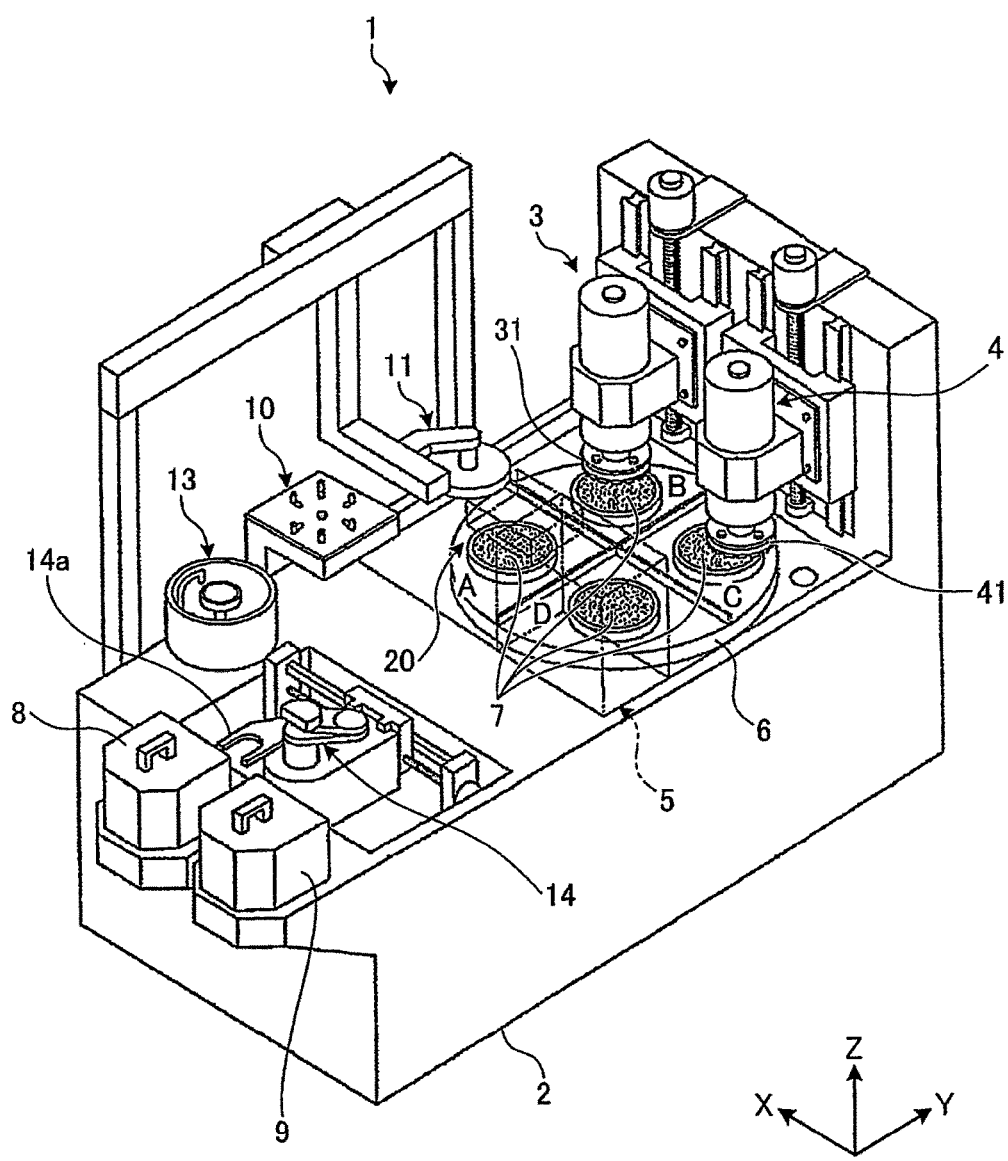
FIG. 2 is a perspective view showing the configuration of a grinding and polishing apparatus for performing the workpiece evaluating method according to the first preferred embodiment.
Figure 3:
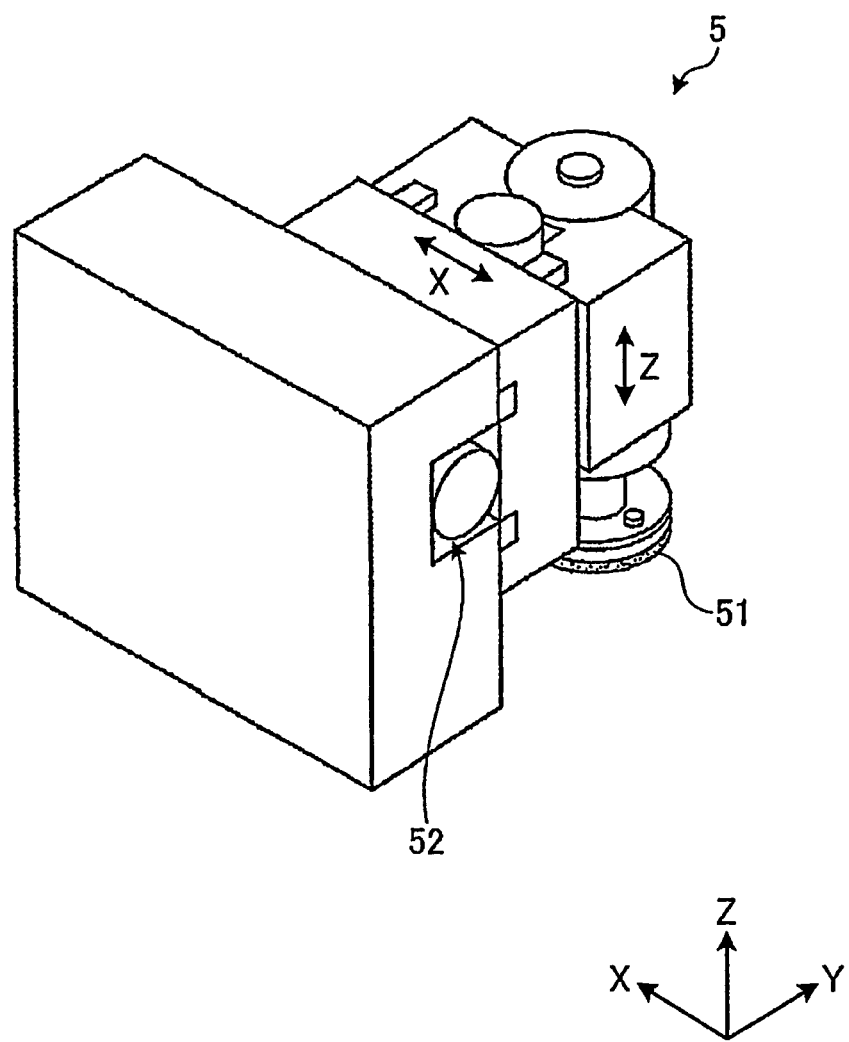
FIG. 3 is a perspective view showing the configuration of polishing means included in the grinding and polishing apparatus shown in FIG. 2.

A workpiece evaluating method according to a first preferred embodiment of the present invention will now be described with reference to the drawings. FIG. 1 is a perspective view showing a device wafer W as a target to be evaluated in the workpiece evaluating method according to the first preferred embodiment. FIG. 2 is a perspective view showing the configuration of a grinding and polishing apparatus 1 for performing the workpiece evaluating method according to the first preferred embodiment. FIG. 3 is a perspective view showing the configuration of polishing means 5 included in the grinding and polishing apparatus 1 shown in FIG. 2.

The workpiece evaluating method (which will be hereinafter referred to simply as evaluating method) according to the first preferred embodiment is a method of evaluating the gettering property of the device wafer W shown in FIG. 1 as a workpiece. As shown in FIG. 1, the device wafer W is a disk-shaped semiconductor wafer or optical device wafer including silicon as a base material. The device wafer W has a front side WS and a back side WR opposite to the front side WS. A plurality of crossing division lines S are formed on the front side WS of the device wafer W to thereby define a plurality of separate regions where a plurality of devices D are formed. That is, the plural devices D are formed on the front side WS of the device wafer W. The back side WR of the device wafer W is ground in the grinding and polishing apparatus 1 to thereby reduce the thickness of the device wafer W to a predetermined thickness. Thereafter, a gettering layer G is formed inside the device wafer W, and the gettering property of the gettering layer G is next evaluated. The gettering property of the gettering layer G means the degree of effectiveness in suppressing the movement of metal elements such as copper harmful to the devices D. Each device D formed on the front side WS of the device wafer W is a memory such as flash memory and dynamic random access memory (DRAM), wherein metal contamination (e.g., contamination by a copper element) from the back side WR is a problem. While the workpiece in the first preferred embodiment is the device wafer W, the workpiece is not limited to the device wafer W in the present invention.

The evaluating method according to the first preferred embodiment is performed by the grinding and polishing apparatus 1 shown in FIG. 2 as a processing system. The grinding and polishing apparatus 1 functions to grind the back side WR of the device wafer W, thereby reducing the thickness of the device wafer W, and also functions to polish the back side WR of the device wafer W ground above, thereby flattening the back side WR with high accuracy and forming the gettering layer G inside the device wafer W. As shown in FIG. 2, the grinding and polishing apparatus 1 includes a base housing 2, first grinding means 3, second grinding means 4, polishing means 5, a turn table 6, a plurality of (e.g., four) holding means 7 provided on the turn table 6, two cassettes 8 and 9, positioning means 10, transfer means 11, cleaning means 13, handling means 14, an evaluating apparatus 20, and control means (not shown).

Each holding means 7 is adapted to selectively take a standby position (load/unload position) A, coarse grinding position B, finish grinding position C, and polishing position D.

The first grinding means 3 includes a vertically extending spindle and a grinding wheel 31 mounted to the lower end of the spindle, wherein the grinding wheel 31 has abrasive members for coarse grinding. The grinding wheel 31 is rotatable about the axis of the spindle and movable in a Z direction parallel to a vertical direction. By rotating the grinding wheel 31 and moving the grinding wheel 31 in the Z direction to press the abrasive members of the grinding wheel 31 against the back side WR of the device wafer W held by the holding means 7 set at the coarse grinding position B, the back side WR of the device wafer W is coarse-ground by the grinding wheel 31 of the first grinding means 3. Similarly, the second grinding means 4 includes a vertically extending spindle and a grinding wheel 41 mounted to the lower end of the spindle, wherein the grinding wheel 41 has abrasive members for finish grinding. The grinding wheel 41 is rotatable about the axis of the spindle and vertically movable in the Z direction. By rotating the grinding wheel 41 and moving the grinding wheel 41 in the Z direction to press the abrasive members of the grinding wheel 41 against the back side WR of the device wafer W (already coarse-ground) held by the holding means 7 set at the finish grinding position C, the back side WR of the device wafer W is finish-ground by the grinding wheel 41 of the second grinding means 4.

As shown in FIG. 3, the polishing means 5 includes a vertically extending spindle and a dry polishing tool 51 such as a polishing pad mounted to the lower end of the spindle, wherein the polishing tool 51 is opposed to the upper surface (holding surface) of the holding means 7 set at the polishing position D. The polishing tool 51 is rotatable about the axis of the spindle and movable in the Z direction. By rotating the polishing tool 51 and moving the polishing tool 51 in the Z direction to press the polishing tool 51 against the back side WR of the device wafer W (already finish-ground) held by the holding means 7 set at the polishing position D, the back side WR of the device wafer W is polished by the polishing tool 51 of the polishing means 5.

The dry polishing tool 51 of the polishing means 5 functions to perform so-called dry polishing to the back side WR of the device wafer W, thereby forming the gettering layer G inside the device wafer W, wherein the gettering layer G includes a strained layer formed by straining a crystal structure. At this time, the die strength of the device wafer W is maintained. In the first preferred embodiment, the die strength of the device wafer W is maintained at 1000 MPa or more. However, the die strength of the device wafer W in the present invention is not limited to this value, but may be set to a value that can provide a desired device strength. As shown in FIG. 3, the polishing means 5 further includes X moving means 52 for moving the polishing tool 51 with the spindle in an X direction perpendicular to the Z direction and parallel to the lateral direction of the base housing 2 shown in FIG. 2.

While the evaluating method according to the first preferred embodiment employs so-called dry polishing for forming the gettering layer G having a gettering property, the present invention may adopt not only this dry polishing, but also any other processing methods capable of forming the gettering layer G having a gettering property (providing strain in a crystal). Examples of such a processing method capable of forming the gettering layer G include grinding using a high-mesh wheel, plasma etching, laser beam application, and ion beam application (see Japanese Patent Laid-open No. 2011-253983, for example). The first grinding means 3, the second grinding means 4, and the polishing means 5 are processing means for processing the device wafer W as a workpiece. Another method as described in Japanese Patent Laid-open No. 2013-244537 may also be used to form the gettering layer G. This method includes the steps of performing wet polishing (e.g., chemical-mechanical polishing (CMP)) as supplying a slurry to thereby remove a grinding strain from the back side WR of the device wafer W, and next wet-polishing the back side WR with a polishing pad as supplying a liquid not containing abrasive grains. As a modification, after polishing the back side WR as supplying the slurry, the supply of the liquid (e.g., pure water) may be stopped or the amount of the liquid to be supplied may be reduced in polishing the back side WR to form the gettering layer G. By stopping the supply of the liquid or reducing the amount of the liquid to be supplied, the device wafer W is heated in polishing the back side WR, so that the gettering layer G can be formed in a short time (these various methods may be used similarly in the other preferred embodiments to be hereinafter described).

Referring back to FIG. 2, the turn table 6 is a disk-shaped table provided on the upper surface of the base housing 2. The turn table 6 is rotatable in a horizontal plane, and it is rotationally driven with predetermined timing. In this preferred embodiment, the four holding means 7 are provided on the turn table 6 so as to be equally spaced at a phase angle of 90 degrees. Each holding means 7 has a chuck table structure with a vacuum chuck formed on the upper surface, wherein the device wafer W placed on the vacuum chuck is held under suction. Each holding means 7 has a vertically extending axis of rotation and it is rotationally driven in a horizontal plane by a rotational drive mechanism (not shown) in grinding and polishing the device wafer W. Each holding means 7 has a holding surface for rotatably holding the device wafer W as a workpiece. By rotating the turn table 6, each holding means 7 is sequentially moved from the standby position A through the coarse grinding position B, the finish grinding position C, and the polishing position D to the standby position A.

Each of the cassettes 8 and 9 functions as a container having a plurality of slots for storing a plurality of device wafers W. The cassette 8 functions to store a plurality of device wafers W before performing the grinding and polishing operation, whereas the cassette 9 functions to store the plural device wafers W after performing the grinding and polishing operation. The positioning means 10 functions as a table for temporarily setting the device wafer W taken out of the cassette 8 and centering the device wafer W.

The transfer means 11 has a suction pad for holding the device wafer W under suction. Before performing the grinding and polishing operation, the transfer means 11 functions to transfer the device wafer W from the positioning means 10 to the standby position A. After performing the grinding and polishing operation, the transfer means 11 functions to transfer the device wafer W from the standby position A to the cleaning means 13.

The handling means 14 is a robot pick having a U-shaped hand 14a for holding the device wafer W under suction and then transferring the same. Before performing the grinding and polishing operation, the handling means 14 functions to transfer the device wafer W from the cassette 8 to the positioning means 10. After performing the grinding and polishing operation, the handling means 14 functions to transfer the device wafer W from the cleaning means 13 to the cassette 9. The cleaning means 13 functions to clean the device wafer W after performing the grinding and polishing operation, thereby removing any contamination such as grinding dust and polishing dust adhering to the work surface (back side WR) of the device wafer W ground and polished. The grinding and polishing apparatus 1 further includes second cleaning means (not shown) provided at the standby position A for cleaning the back side WR of the device wafer W held by the holding means 7 after performing the grinding and polishing operation to form the gettering layer G.

The control means functions to control the above-mentioned components of the grinding and polishing apparatus 1. That is, the control means functions to let the grinding and polishing apparatus 1 perform the processing operation to the device wafer W. More specifically, the control means is provided by a computer capable of executing a computer program. The control means has a processing unit having a microprocessor such as central processing unit (CPU), a storing unit having a memory such as read only memory (ROM) and random access memory (RAM), and an input/output interface unit. The CPU in the control means functions to read out the computer program stored in the ROM, execute the computer program on the RAM, and produce a control signal for controlling the grinding and polishing apparatus 1. The control signal produced is output from the CPU through the input/output interface unit to the components of the grinding and polishing apparatus 1. Further, the control means is connected to display means (not shown) such as a liquid crystal display unit for displaying the condition of the processing operation, images, etc., and also connected to input means to be used by an operator in recording processing information. The input means is configured by at least one of a touch panel provided in the display means and a keyboard.

The evaluating apparatus 20 is an apparatus provided at the standby position A for evaluating the gettering property of the device wafer W in which the gettering layer G has been formed by the grinding and polishing operation. That is, the evaluating apparatus 20 is provided above the holding means 7 set at the standby position A where the grinding means 3 and 4 and the polishing means 5 of the grinding and polishing apparatus 1 are not provided, and functions to determine whether or not the gettering property of the device wafer W ground and polished is good.

Figure 4:
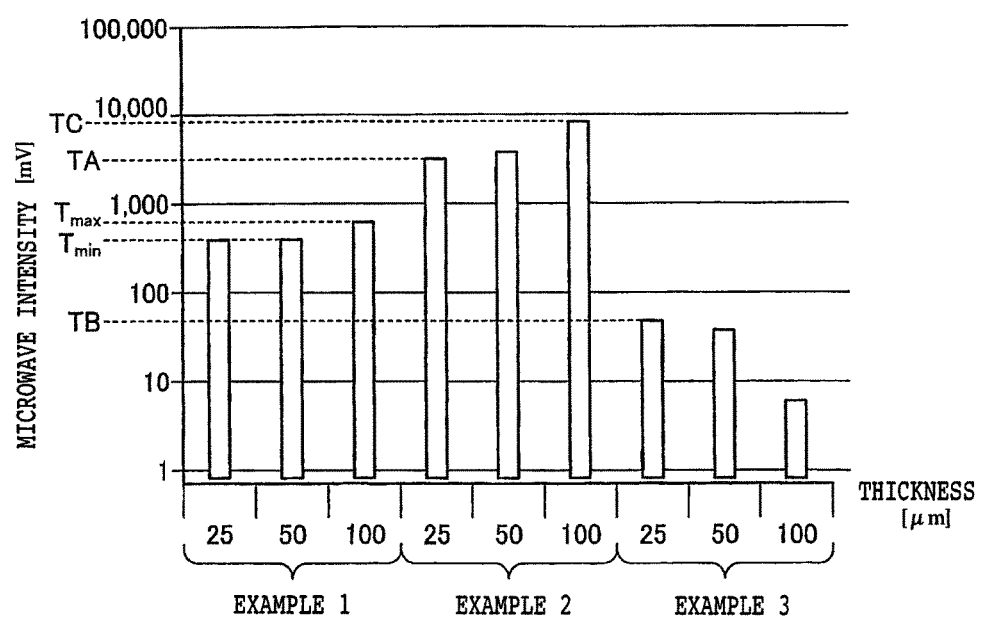
FIG. 4 is a graph showing the intensity of microwaves reflected from the back side of the device wafer shown in FIG. 1, depending on the difference in condition of a gettering layer formed inside the device wafer.

FIG. 4 is a graph showing the intensity of microwaves reflected from the back side WR of the device wafer W shown in FIG. 1, depending on the difference in condition of the gettering layer G formed inside the device wafer W. The present inventors have found that the amount of electrons and holes as excited carriers generated in the device wafer W by the application of excitation light L is different according to the condition (e.g., thickness) of the strained layer, or the gettering layer G formed inside the device wafer W, and that when microwaves MT are applied to the device wafer W, the intensity of microwaves MR reflected from the device wafer W is also different accordingly as shown in FIG. 4. More specifically, the present inventors have found that when the strain in the device wafer W increases, the carriers are less excited (the amount of electrons and holes as the excited carriers is decreased), so that when the microwaves MT are applied to the device wafer W, the intensity of the reflected microwaves MR is reduced.

In view of the above fact, the present inventors have invented the evaluating apparatus 20 for evaluating the gettering property by applying the excitation light L to a part of the back side WR of the device wafer W, measuring the intensity of the microwaves MR reflected from a light applied area R where the excitation light L has been applied, measuring the intensity of the microwaves MR reflected from any area other than the light applied area R, and subtracting the intensity of the microwaves MR reflected from the area other than the light applied area R from the intensity of the microwaves MR reflected from the light applied area R to thereby obtain a differential signal, wherein the gettering property is evaluated according to this differential signal. In FIG. 4, "Example 1," "Example 2," and "Example 3" are different cases obtained by differently processing the device wafer W. In each of Examples 1 to 3, the microwaves MT having a predetermined intensity are applied to the back side WR of the device wafer W, and the excitation light L is applied to the back side WR of the device wafer W in only the light applied area R. Then, the intensity of the microwaves MR reflected from the light applied area R and the intensity of the microwaves MR reflected from the area other than the light applied area R are measured to obtain the differential signal. The wafer in Example 2 is a dummy bare wafer insufficient in gettering property as obtained by performing dry polishing to the device wafer W, that is, a wafer obtained by polishing the device wafer W to remove a grinding damage (wafer having a surface roughness Ra of approximately 1 nm). Accordingly, the wafer in Example 2 has an insufficient gettering property, but has a large die strength.

In contrast, the wafer in Example 3 is a wafer having a thick strained layer as obtained by finish-grinding the back side WR of the device wafer W. That is, the wafer in Example 3 is a wafer not polished, so that it has a large gettering property, but has a small die strength. Accordingly, the wafer in Example 3 has a possibility that when the thickness of the wafer is reduced to 100 µm or less, each device may be damaged in a pickup step. The wafer in Example 1 is a wafer obtained by using the grinding and polishing apparatus 1 to grind the back side WR of the device wafer W and then perform the dry polishing for forming the gettering layer G as maintaining a high die strength (e.g., by the dry polishing using a Gettering DP wheel provided by Disco Corporation). The wafer in Example 1 is also a wafer having a sufficient gettering property confirmed by a conventional inspecting method using forced contamination by copper (a method of contaminating the back side of the wafer with copper and detecting the amount of copper atoms on the front side of the wafer) as described in Japanese Patent Laid-open No. 2012-238731. In each of Examples 1 to 3 shown in FIG. 4, the device wafers W having different thicknesses of 25 µm, 50 µm, and 100 µm are used. In FIG. 4, the vertical axis represents the intensity of microwaves as a differential signal as expressed in a logarithmic scale.

As apparent from FIG. 4, a minimum microwave intensity Tmin in Example 1 (differential signal of the reflection intensity for the wafer having a thickness of 25 µm) is greater than the value five times a maximum microwave intensity TB in Example 3, and a maximum microwave intensity Tmax in Example 1 (differential signal of the reflection intensity for the wafer having a thickness of 100 µm) is less than the value one-fifth times a minimum microwave intensity TA in Example 2 and also less than the value one-tenth times a microwave intensity TC for the wafer having a thickness of 100 µm in Example 2. The present inventors have found that the differential signal related to the intensity of the reflected microwaves depends on the condition of the back side WR of the device wafer W and that whether or not the gettering property of the device wafer W is good can be determined according to the magnitude of the differential signal as an index. That is, as apparent from FIG. 4, the differential signal in Example 2 is high, and the differential signal in Example 3 is low. Accordingly, the lower the gettering property, the higher the differential signal. Conversely, the higher the gettering property, the lower the differential signal.

Figure 5:
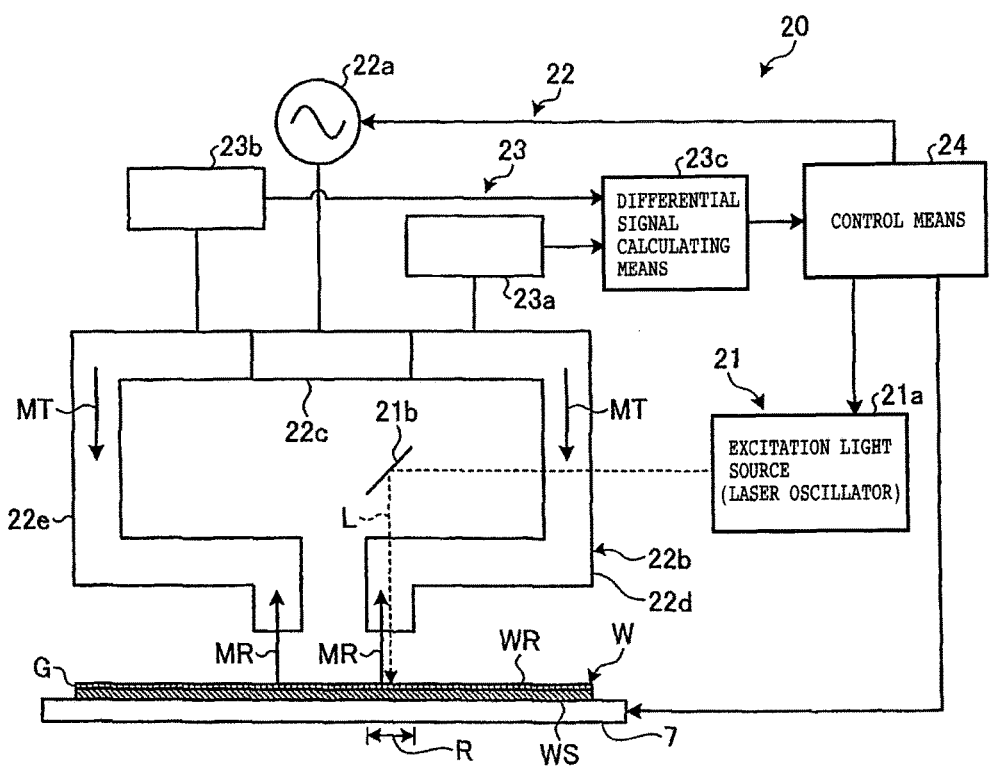
FIG. 5 is a block diagram showing the configuration of an evaluating apparatus included in the grinding and polishing apparatus shown in FIG. 2.

FIG. 5 is a block diagram showing the configuration of the evaluating apparatus 20 in the grinding and polishing apparatus 1 shown in FIG. 2. As shown in FIG. 5, the evaluating apparatus 20 includes excitation light applying means 21, microwave applying means 22, reflected wave receiving means 23, and control means 24.

The excitation light applying means 21 functions to apply excitation light L for exciting carriers (electrons and holes) to a surface layer on the back side WR of the device wafer W. In the first preferred embodiment, the excitation light applying means 21 applies excitation light L having a wavelength of 349 nm, i.e., ultraviolet light, to the device wafer W. However, the wavelength of the excitation light L is not limited to 349 nm in the present invention. The reason why the wavelength of the excitation light L is set to 349 nm in the first preferred embodiment is that light (ultraviolet light) having a short wavelength, e.g., 349 nm, is suitable for the detection of the condition of a crystal (the condition of strain) near the surface layer on the back side WR of the device wafer W. In contrast, light having a long wavelength causes the production of excited carriers (electrons and holes) not only in the surface layer on the back side WR of the device wafer W, but also inside the device wafer W. Accordingly, in contrast to the case of applying light having a short wavelength, e.g., 349 nm, it is undesirable to use light having a long wavelength in accurately detecting the excited condition of the carriers near the surface layer on the back side WR of the device wafer W.

As shown in FIG. 5, the excitation light applying means 21 includes an excitation light source 21a for emitting excitation light L and a mirror 21b for reflecting the excitation light L emitted from the excitation light source 21a toward the device wafer W. The excitation light source 21a is configured by a laser oscillator for radiating ultraviolet light as the excitation light L. The ultraviolet light as the excitation light L is ultraviolet light obtained as a third harmonic of yttrium lithium fluoride (YLF) laser. The excitation light source 21a emits ultraviolet light having a wavelength of 349 nm. The excitation light applying means 21 applies the excitation light L to the back side WR of the device wafer W so as to form a spot having a size sufficiently smaller than the area of the back side WR of the device wafer W. The excitation light L is applied to the back side WR of the device wafer W in a direction perpendicular to the back side WR. The excitation light L is applied to the back side WR of the device wafer W in the area R, which is defined as the light applied area R. Since the wavelength of the excitation light L is 349 nm in the first preferred embodiment, the depth of penetration of the excitation light L into the device wafer W is approximately 10 nm, so that the excitation light applying means 21 can efficiently produce the excited carriers (electrons and holes) in the surface layer on the back side WR of the device wafer W in the light applied area R.

The microwave applying means 22 functions to apply microwaves MT to the light applied area R on the back side WR of the device wafer W and also to any area other than the light applied area R on the back side WR of the device wafer W. The microwave applying means 22 includes a microwave oscillator 22a for oscillating microwaves MT, an amplifier (not shown) for amplifying the microwaves MT oscillated by the microwave oscillator 22a, and a waveguide member 22b.

The microwave oscillator 22a functions to output (emit) microwaves MT. In the first preferred embodiment, the microwave oscillator 22a outputs microwaves MT having a frequency of 26 GHz. However, the frequency of the microwaves MT is not limited to 26 GHz in the present invention.

The amplifier is provided between the microwave oscillator 22a and the waveguide member 22b and functions to amplify the microwaves MT output from the microwave oscillator 22a. The waveguide member 22b includes dividing means 22c for dividing the microwaves MT amplified by the amplifier into two parts and a pair of first and second waveguides 22d and 22e provided between the dividing means 22c and the device wafer W. The first waveguide 22d is opposed to the light applied area R on the back side WR of the device wafer W in the direction perpendicular to the back side WR. The first waveguide 22d transmits the microwaves MT so as to apply them to the light applied area R. The second waveguide 22e is opposed to the area other than the light applied area R on the back side WR of the device wafer W in the direction perpendicular to the back side WR. The second waveguide 22e transmits the microwaves MT so as to apply them to the area other than the light applied area R.

The reflected wave receiving means 23 functions as measuring means for measuring the intensity of microwaves MR reflected from the light applied area R and the intensity of microwaves MR reflected from the area other than the light applied area R and then subtracting the intensity of the microwaves MR reflected from the area other than the light applied area R from the intensity of the microwaves MR reflected from the light applied area R to thereby obtain a differential signal. The reflected wave receiving means 23 includes a first receiver 23a, a second receiver 23b, and differential signal calculating means 23c. The first receiver 23a receives the microwaves MR reflected from the light applied area R, measures the intensity of the microwaves MR received, and outputs the intensity measured to the differential signal calculating means 23c. Similarly, the second receiver 23b receives the microwaves MR reflected from the area other than the light applied area R, measures the intensity of the microwaves MR received, and outputs the intensity measured to the differential signal calculating means 23c.

The differential signal calculating means 23c subtracts the intensity of the microwaves MR measured by the second receiver 23b from the intensity of the microwaves MR measured by the first receiver 23a to thereby obtain a differential signal as a difference in intensity of the reflected microwaves MR between in the light applied area R and in the other area on the back side WR of the device wafer W. The differential signal thus obtained is output to the control means 24. The function of the differential signal calculating means 23c is realized by a CPU for executing at least one of software and firmware or by a processing circuit configured by at least one circuit.

The control means 24 functions to control the above-mentioned components of the evaluating apparatus 20. That is, the control means 24 functions to let the evaluating apparatus 20 perform the evaluating method of evaluating the gettering property according to the first preferred embodiment.

The control means 24 functions to determine whether or not the gettering property of the gettering layer G formed in the device wafer W is good according to the intensity of the differential signal input from the differential signal calculating means 23c. More specifically, when the intensity of the differential signal input from the differential signal calculating means 23c is less than or equal to an upper limit preset according to the microwave intensity Tmax in Example 1 shown in FIG. 4, the control means 24 determines that the gettering property of the gettering layer G is good. Further, when the intensity of the differential signal input from the differential signal calculating means 23c is greater than or equal to a lower limit preset according to the microwave intensity Tmin in Example 1 shown in FIG. 4, the control means 24 determines that the die strength of the device wafer W is good. Conversely, when the intensity of the differential signal input from the differential signal calculating means 23c is less than the above-mentioned lower limit or greater than the above-mentioned upper limit, the control means 24 determines that the gettering property of the gettering layer G is bad or that the die strength of the device wafer W is low. Thusly, the control means 24 compares the intensity of the differential signal input from the differential signal calculating means 23c with the lower limit and the upper limit mentioned above in evaluating the gettering property of the gettering layer G formed in the actual device wafer W.

While the control means 24 of the evaluating apparatus 20 according to the first preferred embodiment is adapted to determine processing conditions including the gettering property according to the lower limit and the upper limit of the intensity of the differential signal, only the gettering property may be determined by the control means 24 according to only the upper limit of the intensity without using the lower limit of the intensity. In this case, when the intensity of the differential signal input from the differential signal calculating means 23c is less than or equal to the upper limit preset according to the microwave intensity Tmax shown in FIG. 4, the control means 24 determines that the gettering property of the gettering layer G is good, whereas when the intensity of the differential signal is greater than the above-mentioned upper limit, the control means 24 determines that the gettering property of the gettering layer G is bad. Thusly, the control means 24 may compare the intensity of the differential signal input from the differential signal calculating means 23c with only the upper limit. As a modification, the criterion of determination of whether or not the gettering property is good may be set so that the intensity of the differential signal must be greater than the value (lower limit) five times the maximum microwave intensity TB in Example 3 and less than the value (upper limit) one-fifth times the minimum microwave intensity TA in Example 2.

The lower limit and the upper limit of the intensity may be suitably set according to the gettering property required in the gettering layer G to be formed in the device wafer W. For example, the lower limit may be set to the microwave intensity Tmin in consideration of the gettering property required in the gettering layer G. The upper limit may be set to the microwave intensity Tmax in consideration of the gettering property required in the gettering layer G. Further, the lower limit and the upper limit of the intensity may be set to the microwave intensity ±10% in Example 1, i.e., the differential signal intensity +10% and the differential signal intensity −10%, respectively, in Example 1. Further, the upper limit and the lower limit may be set according to the thickness of the device wafer W.

The control means 24 is configured by a computer capable of executing a computer program. The control means 24 includes a processing unit having a microprocessor such as CPU, a storing unit having a memory such as ROM and RAM, and an input/output interface unit.

The CPU in the control means 24 functions to read out the computer program stored in the ROM, execute the computer program on the RAM, and produce a control signal for controlling the evaluating apparatus 20. The control signal produced is output from the CPU through the input/output interface unit to the components of the evaluating apparatus 20.

There will now be described the processing operation of the grinding and polishing apparatus 1 and an evaluating method according to the first preferred embodiment. The evaluating method according to the first preferred embodiment is a method of evaluating the gettering property of the device wafer W after forming the gettering layer G inside the device wafer W.

First, the operator mounts the cassette 8 storing plural device wafers W to be ground and polished on the base housing 2 and also mounts the cassette 9 storing no device wafers W on the base housing 2. Thereafter, the operator records processing information into the control means (not shown) of the grinding and polishing apparatus 1. When the control means of the grinding and polishing apparatus 1 is instructed by the operator to start a processing operation, the grinding and polishing apparatus 1 is operated to start the processing operation. In the processing operation, one of the device wafers W is taken out of the cassette 8 by the handling means 14 and next transferred to the positioning means 10 by the handling means 14. The device wafer W is next centered by the positioning means 10. Thereafter, the device wafer W is transferred from the positioning means 10 to the holding means 7 set at the standby position A by operating the transfer means 11. The device wafer W is held by the holding means 7, and the turn table 6 is rotated to sequentially move the device wafer W to the coarse grinding position B, the finish grinding position C, the polishing position D, and the standby position A. Every time the turn table 6 is rotated 90 degrees, another one of the device wafers W to be ground and polished is transferred to the holding means 7 set at the standby position A.

At the coarse grinding position B, the back side WR of the device wafer W is coarse-ground by the first grinding means 3. Thereafter, at the finish grinding position C, the back side WR of the device wafer W is finish-ground by the second grinding means 4. Thereafter, at the polishing position D, the back side WR of the device wafer W is polished by the polishing means 5, thereby forming the gettering layer G inside the device wafer W. Thereafter, the device wafer W is set at the standby position A, and the back side WR of the device wafer W is cleaned by the second cleaning means (not shown) to remove processing dust from the back side WR. Thereafter, the device wafer W is subjected to the evaluating method using the evaluating apparatus 20.

The evaluating method includes an excitation light applying step, a microwave applying step, a measuring step, and a gettering property determining step. The excitation light applying step is performed by the excitation light applying means 21 of the evaluating apparatus 20 in such a manner that the excitation light L is applied to the light applied area R on the back side WR of the device wafer W. The microwave applying step is performed by the microwave applying means 22 of the evaluating apparatus 20 in such a manner that while the excitation light L is being applied, the microwaves MT are applied to the light applied area R and also to the area other than the light applied area R on the back side WR of the device wafer W. The measuring step is performed by the reflected wave receiving means 23 of the evaluating apparatus 20 in the following manner.

The intensity of the microwaves MR reflected from the light applied area R on the back side WR of the device wafer W is measured by the first receiver 23*a* of the reflected wave receiving means 23. Similarly, the intensity of the microwaves MR reflected from the area other than the light applied area R on the back side WR of the device wafer W is measured by the second receiver 23*b* of the reflected wave receiving means 23. Thereafter, the intensity of the microwaves MR reflected from the area other than the light applied area R is subtracted from the intensity of the microwaves MR reflected from the light applied area R by the differential signal calculating means 23*c* of the reflected wave receiving means 23, thereby obtaining a differential signal. The differential signal thus obtained is output to the control means 24.

The gettering property determining step is performed by the control means 24 in such a manner that the gettering property of the device wafer W is determined according to the intensity of the differential signal obtained in the measuring step. More specifically, when the intensity of the differential signal is less than or equal to the upper limit, the control means 24 determines that the gettering property of the gettering layer G is good (proper). Further, when the intensity of the differential signal is greater than or equal to the lower limit, the control means 24 determines that the die strength is also sufficient (proper). Conversely, when the intensity of the differential signal is greater than the upper limit, the control means 24 determines that the gettering property of the gettering layer G is bad (insufficient). Further, when the intensity of the differential signal is less than the lower limit, the control means 24 determines that the die strength is insufficient.

After evaluating the gettering property of the device wafer W set at the standby position A, the device wafer W is transferred to the cleaning means 13 by the transfer means 11. Thereafter, the device wafer W is cleaned by the cleaning means 13 and then transferred to the cassette 9 by the handling means 14.

According to the processing operation of the grinding and polishing apparatus 1, i.e., the evaluating method according to the first preferred embodiment, the gettering property is determined according to the differential signal as the difference between the intensity of the microwaves MR reflected from the light applied area R where the excitation light L has been applied and the intensity of the microwaves MR reflected from the area other than the light applied area R. Accordingly, the determination of whether or not the gettering property is good can be made without contaminating the device wafer W with metal elements in the evaluating method according to the first preferred embodiment. That is, the gettering property of the device wafer W that may become a product can be evaluated by the evaluating method according to the first preferred embodiment.

Since the gettering property is determined according to the differential signal in the evaluating method according to the first preferred embodiment, noise can be removed in real time, so that whether or not the gettering property is good can be accurately determined. Further, since the gettering property is determined by using the intensity of the microwaves MR reflected from the light applied area R and the intensity of the microwaves MR reflected from the area other than the light applied area R in the evaluating method according to the first preferred embodiment, the determination of whether or not the gettering property is good can be made without the need for any complicated calculation process.

Further, since the excitation light L having a wavelength of 349 nm is applied in the evaluating method according to the first preferred embodiment, the carriers present in the vicinity of the back side WR of the device wafer W can be excited, so that the gettering property of the gettering layer G can be accurately determined.

In the gettering property determining step, the evaluating apparatus 20 according to the first preferred embodiment determines the gettering property in the following manner. That is, when the intensity of the differential signal is less than or equal to the upper limit, it is determined that the gettering property of the gettering layer G is good (proper). Further, when the intensity of the differential signal is greater than or equal to the lower limit, it is determined that the die strength is also sufficient (proper).

As a modification, the control means 24 of the evaluating apparatus 20 may compare the differential signal obtained from the device wafer W as a target with a differential signal obtained from a device wafer W (reference wafer) having a reference gettering property, thereby evaluating the gettering property of the target device wafer W. That is, the control means 24 of the evaluating apparatus 20 may store and set the range including a differential signal value (reference differential signal value) obtained by applying microwaves to the reference wafer and receiving reflected microwaves, as "range (proper range) where a proper gettering property and a proper die strength can be obtained." In this case, the control means 24 determines the gettering property and the die strength in the following manner. That is, when the differential signal value obtained from the target device wafer W falls within the proper range where the reference differential signal value is set, it is determined that the gettering property and the die strength are sufficient (proper). Conversely, when the differential signal value obtained from the target device wafer W does not fall within the proper range where the reference differential signal value is set, it is determined that either the gettering property or the dis strength is insufficient. The reference wafer may be a wafer having a sufficient gettering property confirmed by a conventional inspection method using forced contamination with copper as described in Japanese Patent Laid-open No. 2012-238731, for example (a method of contaminating the back side of the wafer with copper and detecting the amount of copper atoms on the front side of the wafer). Alternatively, the reference wafer may be a wafer processed similarly to the above wafer having a sufficient gettering property confirmed.

For example, the proper range may be set to a range from the reference differential signal value −20% to the reference differential signal value +20%. Further, the proper range may be set to a range obtained from a standard deviation (a) of the reference differential signal value (e.g., a range from the reference differential signal value −3σ to the reference differential signal value +3σ). Further, the upper limit and the lower limit of the proper range may be arbitrarily set according to the priority between the gettering property and the die strength. For example, when the gettering property has a priority over the die strength, the upper limit of the proper range may be set to the reference differential signal value +10%, and the lower limit of the proper range may be set to the reference differential signal value −20%. Conversely, when the die strength has a priority over the gettering property, the lower limit of the proper range may be set to the reference differential signal value −10%, and the upper limit of the proper range may be set to the reference differential signal value +20%. Further, only the upper limit may be set in consideration of only the gettering property.

Second Preferred Embodiment

Figure 6:
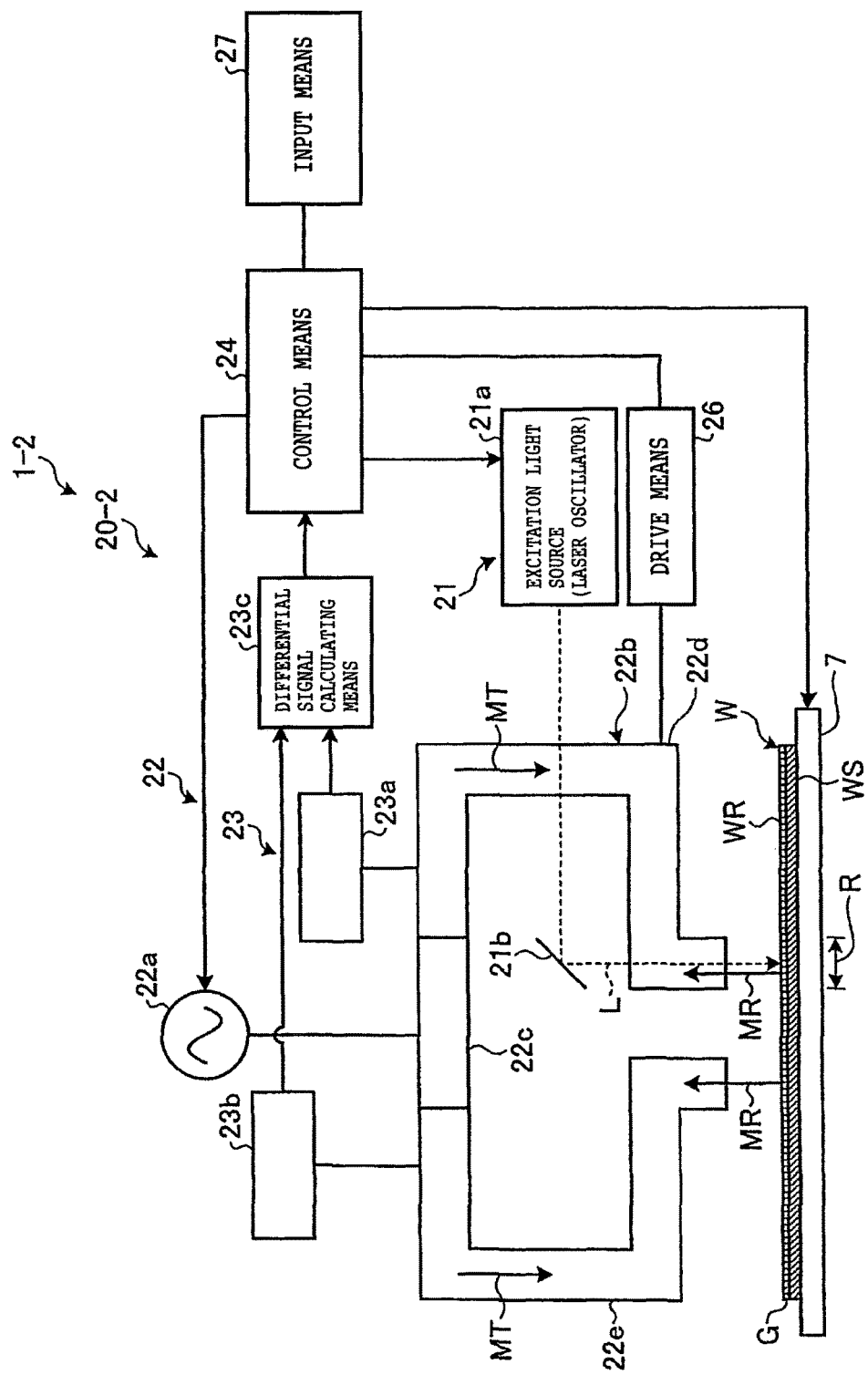
FIG. 6 is a block diagram showing the configuration of an evaluating apparatus included in a grinding and polishing apparatus for performing a workpiece evaluating method according to a second preferred embodiment of the present invention.
Figure 7:
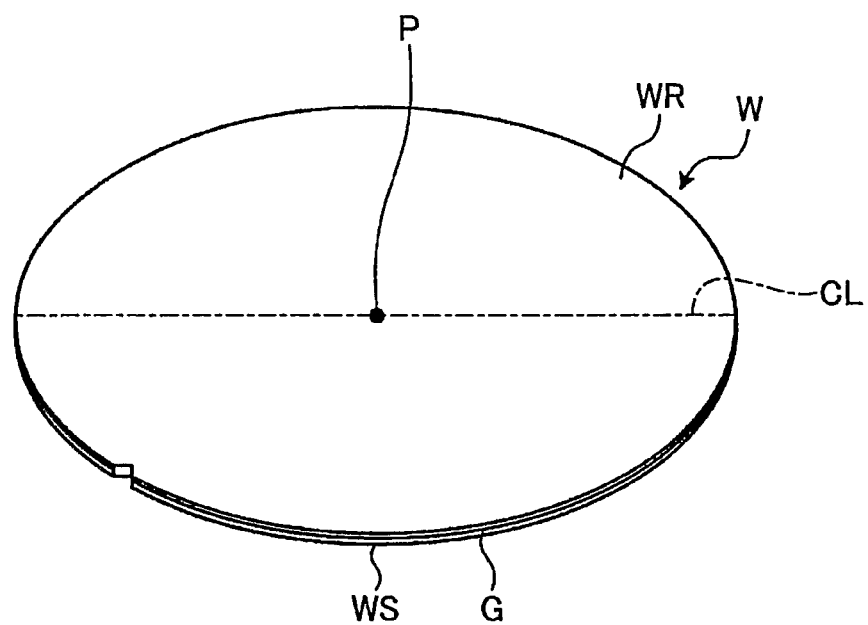
FIG. 7 is a perspective view showing a measurement position on a device wafer where a reference differential signal value is measured by the evaluating apparatus shown in FIG. 6.

An evaluating method according to a second preferred embodiment of the present invention will now be described with reference to the drawings. FIG. 6 is a block diagram showing the configuration of an evaluating apparatus 20-2 in a grinding and polishing apparatus 1-2 for performing the workpiece evaluating method according to the second preferred embodiment. FIG. 7 is a perspective view showing a measurement position on a device wafer W where a reference differential signal value is measured by the evaluating apparatus 20-2 shown in FIG. 6. In FIGS. 6 and 7, the same parts as those of the first preferred embodiment are denoted by the same reference symbols, and the description thereof will be omitted.

As shown in FIG. 6, the evaluating apparatus 20-2 in the grinding and polishing apparatus 1-2 as a processing system according to the second preferred embodiment includes excitation light applying means 21, microwave applying means 22, reference wave receiving means 23, control means 24, drive means 26, and input means 27. The drive means 26 functions to relatively move the microwave applying means 22 and the device wafer W held by the holding means 7 set at the standby position A.

More specifically, the drive means 26 is adapted to move the microwave applying means 22 relative to the device wafer W held by the holding means 7 set at the standby position A, so as to obtain the intensity of microwaves reflected from a center line CL passing through the center P on the back side WR of the device wafer W shown in FIG. 7 in the condition where the device wafer W is held by the holding means 7 set at the standby position A. Accordingly, a differential signal is obtained along the center line CL of the device wafer W. In other words, the drive means 26 is adapted to move the microwave applying means 22 along the center line CL on the back side WR of the device wafer W depicted in FIG. 7 held by the holding means 7 set at the standby position A. The drive means 26 includes a motor, a lead screw for moving the microwave applying means 22 by using a rotational drive force of the motor, and a linear guide for guiding the moving direction of the microwave applying means 22. The configuration of the drive means 26 is not limited to the above configuration including the motor, lead screw, and linear guide.

The input means 27 is connected to the control means 24. The input means 27 functions to input into the control means 24 the position on the center line CL of the device wafer W held by the holding means 7 set at the standby position A, i.e., the range of movement of the microwave applying means 22 along the center line CL. In other words, the input means 27 functions to input into the control means 24 a differential signal obtaining position on the center line CL of the device wafer W held by the holding means 7 set at the standby position A. More specifically, in the second preferred embodiment, the input means 27 is adapted to input into the control means 24 a plurality of positions as the differential signal obtaining position on the center line CL of the device wafer W held by the holding means 7 set at the standby position A. The input means 27 is configured by at least one of a touch panel and a keyboard.

In the measuring step to be performed by the evaluating apparatus 20-2, the microwave applying means 22 is moved along the center line CL by the drive means 26 controlled by the control means 24. During the movement of the microwave applying means 22, the intensity of microwaves reflected from the light applied area R and the intensity of microwaves reflected from the area other than the light applied area R are measured at the plural positions input from the input means 27. Thereafter, a differential signal is calculated at each position in a manner similar to that of the first preferred embodiment. In the gettering property determining step to be performed by the evaluating apparatus 20-2, the control means 24 determines whether or not the intensity of the differential signal at each position on the center line CL falls within the proper range, and then stores the result of determination of whether or not the gettering property at each position is proper.

By operating the processing system 1-2, i.e., by performing the evaluating method according to the second preferred embodiment, the determination of whether or not the gettering property is good can be made without contaminating the device wafer W with metal elements.

Further, in the processing system 1-2, i.e., in the evaluating method according to the second preferred embodiment, while the microwave applying means 22 is being moved relative to the device wafer W, the control means 24 calculates the differential signal at the plural positions input from the input means 27 and then determines whether or not the gettering property at the plural positions is proper. That is, according to the second preferred embodiment, the determination of whether or not the gettering property is good can be made at the plural positions on the device wafer W, so that this determination can be made for each device D. In general, the gettering property of the device wafer W tends to differ (vary) in the radial direction of the device wafer W. Accordingly, by moving the microwave applying means 22 relative to the device wafer W along the center line CL thereof in obtaining the differential signal from the differential signal calculating means 23c according to the second preferred embodiment, it is possible to estimate whether or not the gettering property of the whole of the device wafer W is good. In this preferred embodiment, the proper range is defined by the upper limit and the lower limit of the differential signal obtained from FIG. 4 and the gettering property is determined according to whether or not the intensity of the differential signal falls within this proper range. However, the configuration of this preferred embodiment is not limited to the above. For example, excitation light and microwaves may be applied to the whole surface or plural points of a reference wafer having a good gettering property confirmed to thereby calculate a differential signal at each point of the reference wafer and then define a proper range (as a criterion of determination of whether or not the gettering property is proper) according to the differential signal calculated above.

Third Preferred Embodiment

Figure 8A:
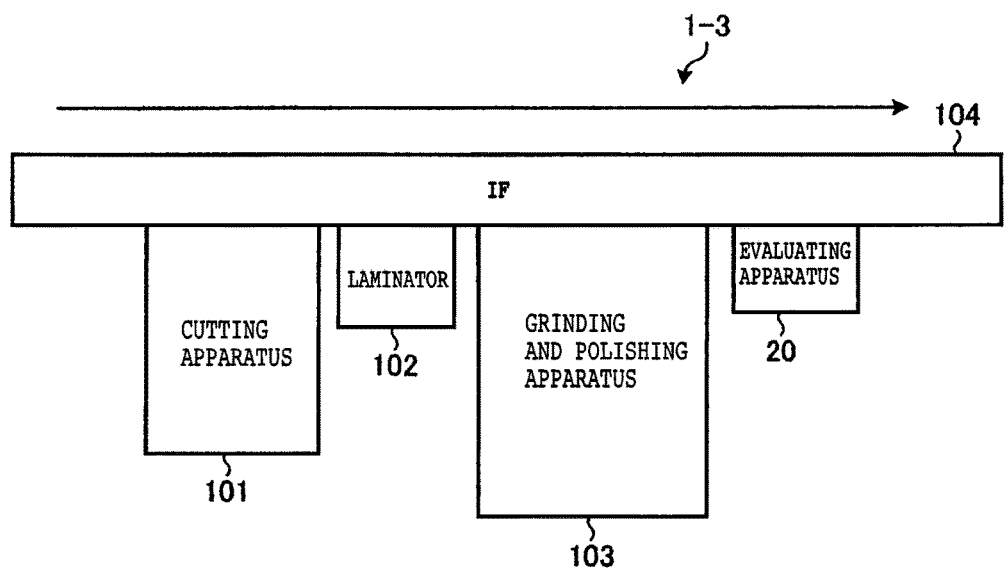
FIG. 8A is a schematic plan view showing a processing system for performing a workpiece evaluating method according to a third preferred embodiment of the present invention.
Figure 8B:
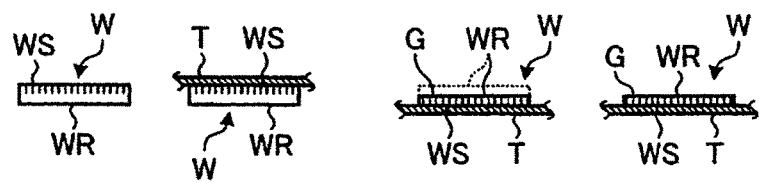
FIG. 8B is a schematic sectional view showing a series of process steps to be performed by the processing system shown in FIG. 8A.

An evaluating method according to a third preferred embodiment of the present invention will now be described with reference to the drawings. FIG. 8A is a schematic plan view showing a processing system 1-3 for performing the workpiece evaluating method according to the third preferred embodiment. FIG. 8B is a schematic sectional view showing a series of process steps to be performed by the processing system 1-3 shown in FIG. 8A. In FIGS. 8A and 8B, the same parts as those of the first preferred embodiment are denoted by the same reference symbols, and the description thereof will be omitted.

As shown in FIG. 8A, the processing system 1-3 according to the third preferred embodiment includes a cutting apparatus 101, a laminator 102, a grinding and polishing apparatus 103 for processing a device wafer W as imparting a gettering property to the device wafer W, an evaluating apparatus 20, and an interface 104 expressed as IF in FIG. 8A. As shown in FIG. 8B, the cutting apparatus 101 functions to half-cut the device wafer W as a workpiece along each division line S from the front side WS to the depth greater than or equal to a finished thickness. The laminator 102 functions to attach a protective tape T to the front side WS of the device wafer W half-cut along each division line S. The grinding and polishing apparatus 103 includes the first grinding means 3, the second grinding means 4, and the polishing means 5 used in the first preferred embodiment and functions to grind and polish the back side WR of the device wafer W half-cut along each division line S, thereby dividing the device wafer W into the devices D and also forming a gettering layer G inside each device D. The evaluating apparatus 20 is an apparatus for determining whether or not the gettering property of the gettering layer G is good. The device wafer W is adapted to be sequentially transferred in the order of the cutting apparatus 101, the laminator 102, the grinding and polishing apparatus 103, and the evaluating apparatus 20 through the interface 104.

As similar to the first preferred embodiment, by operating the processing system 1-3, i.e., by performing the evaluating method according to the third preferred embodiment, the determination of whether or not the gettering property is good can be made without contaminating the device wafer W with metal elements.

While the processing system 1-3 according to the third preferred embodiment employs the grinding and polishing apparatus 103 for performing dry polishing to form the gettering layer G having a gettering property, the present invention may adopt not only such a dry polishing apparatus, but also any other apparatuses for performing a processing method capable of forming the gettering layer G having a gettering property (providing strain in a crystal). Examples of such an apparatus for performing a processing method capable of forming the gettering layer G include a grinding apparatus for grinding the device wafer W by using a high-mesh wheel, an apparatus for performing plasma etching to the device wafer W after polishing, an apparatus for performing laser beam application, and an apparatus for performing ion beam application (see Japanese Patent Laid-open No. 2011-253983, for example).

Fourth Preferred Embodiment

Figure 9:
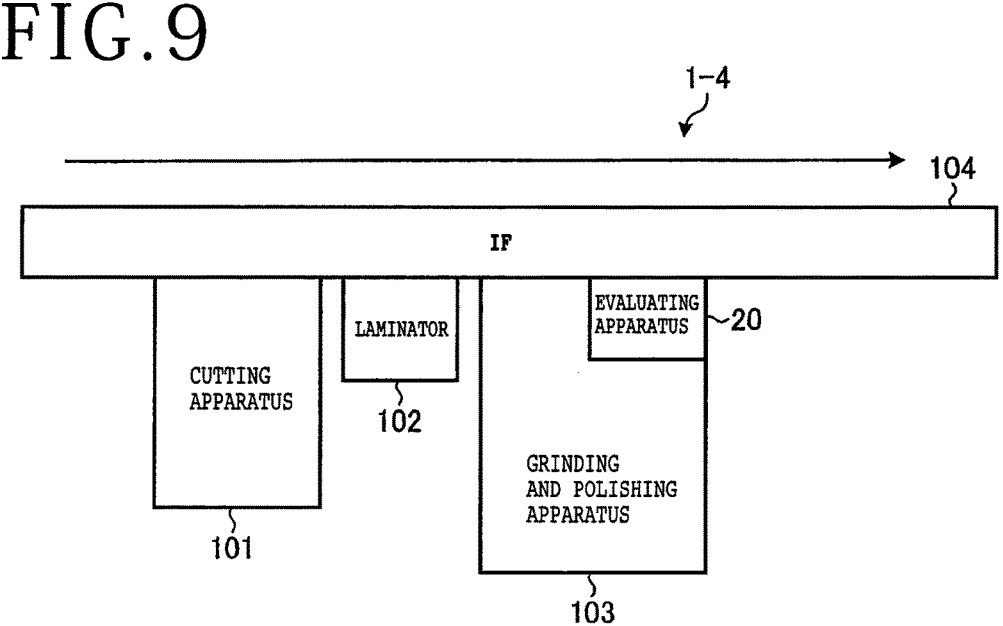
FIG. 9 is a schematic plan view showing a processing system for performing a workpiece evaluating method according to a fourth preferred embodiment of the present invention.

An evaluating method according to a fourth preferred embodiment of the present invention will now be described with reference to the drawings. FIG. 9 is a schematic plan view showing a processing system 1-4 for performing the workpiece evaluating method according to the fourth preferred embodiment. In FIG. 9, the same parts as those of the third preferred embodiment are denoted by the same reference symbols, and the description thereof will be omitted.

As shown in FIG. 9, the configuration of the processing system 1-4 according to the fourth preferred embodiment is the same as the configuration of the processing system 1-3 according to the third preferred embodiment except that the evaluating apparatus 20 is included in the grinding and polishing apparatus 103 as a gettering property imparting apparatus.

As similar to the third preferred embodiment, by operating the processing system 1-4, i.e., by performing the evaluating method according to the fourth preferred embodiment, the determination of whether or not the gettering property is good can be made without contaminating the device wafer W with metal elements. Further, as similar to the third preferred embodiment, examples of an apparatus for performing a processing method capable of forming the gettering layer G include a grinding apparatus for grinding the device wafer W by using a high-mesh wheel, an apparatus for performing plasma etching to the device wafer W after polishing, an apparatus for performing laser beam application, and an apparatus for performing ion beam application (see Japanese Patent Laid-open No. 2011-253983, for example). Further, as similar to the first preferred embodiment, wet polishing can be used as the processing for imparting a gettering property to the device wafer W.

Further, in each of the processing systems 1-3 and 1-4 according to the third and fourth preferred embodiments, the cutting apparatus 101 may be replaced by a laser processing apparatus for forming a modified layer inside the device wafer W.

Fifth Preferred Embodiment

Figure 10:
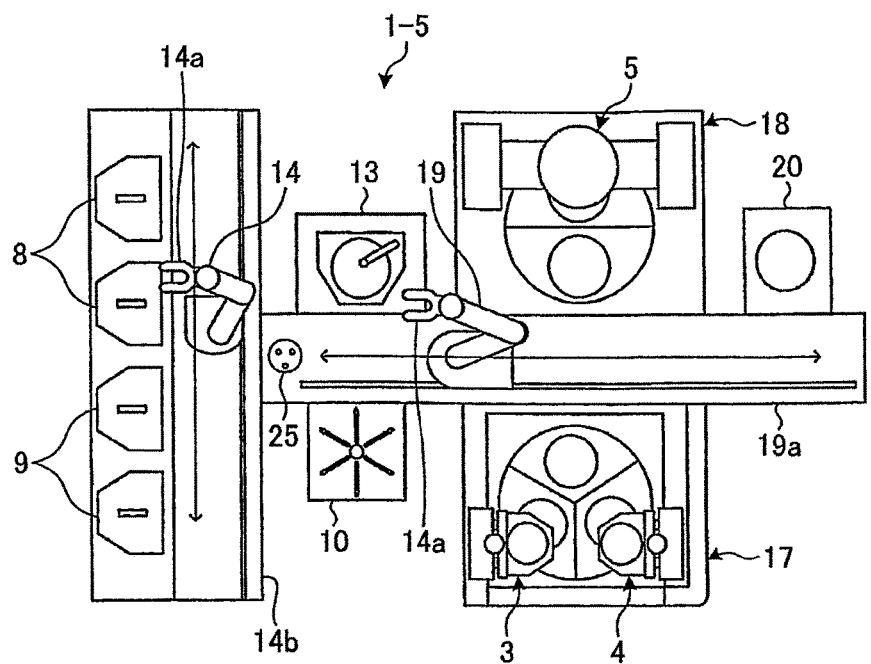
FIG. 10 is a plan view showing a processing system for performing a workpiece evaluating method according to a fifth preferred embodiment of the present invention.

An evaluating method according to a fifth preferred embodiment of the present invention will now be described with reference to the drawings. FIG. 10 is a plan view showing a processing system 1-5 for performing the workpiece evaluating method according to the fifth preferred embodiment. In FIG. 10, the same parts as those of the first preferred embodiment are denoted by the same reference symbols, and the description thereof will be omitted.

As shown in FIG. 10, the processing system 1-5 according to the fifth preferred embodiment includes two cassettes 8 and two cassettes 9 arranged in a line. Handling means 14 having a U-shaped hand 14a is movably supported by a moving and supporting mechanism 14b so as to be movable along the line of the cassettes 8 and 9. The processing system 1-5 includes transfer means 19 having a U-shaped hand 14a similar to that of the handling means 14. That is, the transfer means 19 is configured by a robot pick similar to the handling means 14. The transfer means 19 is movably supported by a moving and supporting mechanism 19a so as to be movable in a direction perpendicular to the moving direction of the handling means 14. Positioning means 10 and cleaning means 13 are mounted at one end portion of the moving and supporting mechanism 19a near the cassettes 8 and 9. A grinding apparatus 17 having first grinding means 3 and second grinding means 4 and a polishing apparatus 18 having polishing means 5 are mounted at a central portion of the moving and supporting mechanism 19a. An evaluating apparatus 20 is mounted at the other end portion of the moving and supporting mechanism 19a so as to be spaced apart from the cassettes 8 and 9.

A temporary setting portion 25 is provided at one end portion of the moving and supporting mechanism 19a. In operation, the device wafer W is transferred from any one of the two cassettes 8 to the temporary setting portion 25 by operating the handling means 14. Thereafter, the device wafer W is transferred from the temporary setting portion 25 to the positioning means 10 by operating the transfer means 19. Thereafter, the device wafer W is sequentially transferred from the positioning means 10 through the grinding apparatus 17, the polishing apparatus 18, and the evaluating apparatus 20 in this order to the cleaning means 13 by operating the transfer means 19. In the grinding apparatus 17, the device wafer W is coarse-ground by the first grinding means 3 and next finish-ground by the second grinding means 4. In the polishing apparatus 18, the device wafer W is polished. In the evaluating apparatus 20, the gettering property of the device wafer W is evaluated. The device wafer W is next cleaned by the cleaning means 13. Thereafter, the device wafer W is transferred to the temporary setting portion 25 by operating the transfer means 19 and next transferred to any one of the two cassettes 9 by operating the handling means 14.

As similar to the first preferred embodiment, by operating the processing system 1-5, i.e., by performing the evaluating method according to the fifth preferred embodiment, the determination of whether or not the gettering property is good can be made without contaminating the device wafer W with metal elements. Further, as similar to the first preferred embodiment, the processing system 1-5 according to the fifth preferred embodiment employs so-called dry polishing for forming the gettering layer G having a gettering property. However, this preferred embodiment may adopt not only this dry polishing, but also any other processing methods capable of forming the gettering layer G having a gettering property. Examples of such a processing method include grinding using a high-mesh wheel, plasma etching after polishing the device wafer W, laser beam application, and ion beam application (see Japanese Patent Laid-open No. 2011-253983, for example). As similar to the first preferred embodiment, wet polishing may also be used. Further, the temporary setting portion 25 may be omitted and the device wafer W may be directly transferred between the handling means 14 and the transfer means 19.

Sixth Preferred Embodiment

Figure 11:
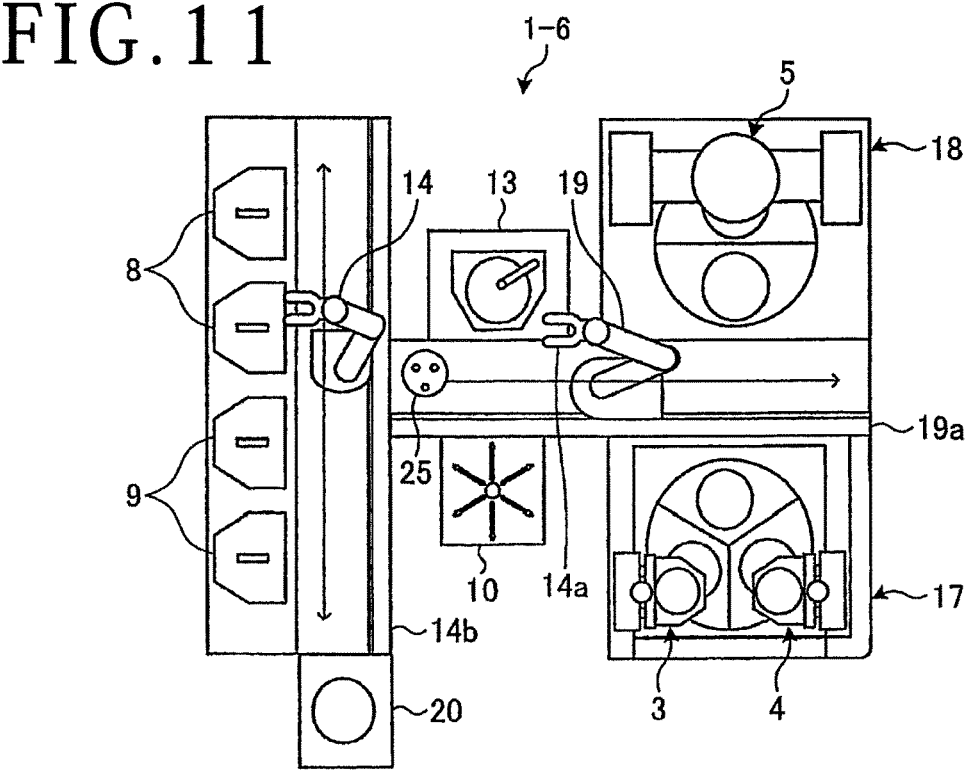
FIG. 11 is a plan view showing a processing system for performing a workpiece evaluating method according to a sixth preferred embodiment of the present invention.

An evaluating method according to a sixth preferred embodiment of the present invention will now be described with reference to the drawings. FIG. 11 is a plan view showing a processing system 1-6 for performing the workpiece evaluating method according to the sixth preferred embodiment. In FIG. 11, the same parts as those of the fifth preferred embodiment are denoted by the same reference symbols, and the description thereof will be omitted.

As shown in FIG. 11, the configuration of the processing system 1-6 according to the sixth preferred embodiment is the same as the configuration of the processing system 1-5 according to the fifth preferred embodiment except that the evaluating apparatus 20 is mounted at one end of the moving and supporting mechanism 14b for movably supporting the handling means 14 to evaluate the gettering property after cleaning the device wafer W.

As similar to the first preferred embodiment, by operating the processing system 1-6, i.e., by performing the evaluating method according to the sixth preferred embodiment, the determination of whether or not the gettering property is good can be made without contaminating the device wafer W with metal elements. Further, as similar to the first preferred embodiment, the processing system 1-6 according to the sixth preferred embodiment employs so-called dry polishing for forming the gettering layer G having a gettering property. However, this preferred embodiment may adopt not only this dry polishing, but also any other processing methods capable of forming the gettering layer G having a gettering property. Examples of such a processing method include grinding using a high-mesh wheel, plasma etching after polishing the device wafer W, laser beam application, and ion beam application (see Japanese Patent Laid-open No. 2011-253983, for example). As similar to the first preferred embodiment, wet polishing may also be used.

Further, the temporary setting portion 25 may be omitted and the device wafer W may be directly transferred between the handling means 14 and the transfer means 19.

Seventh Preferred Embodiment

Figure 12:
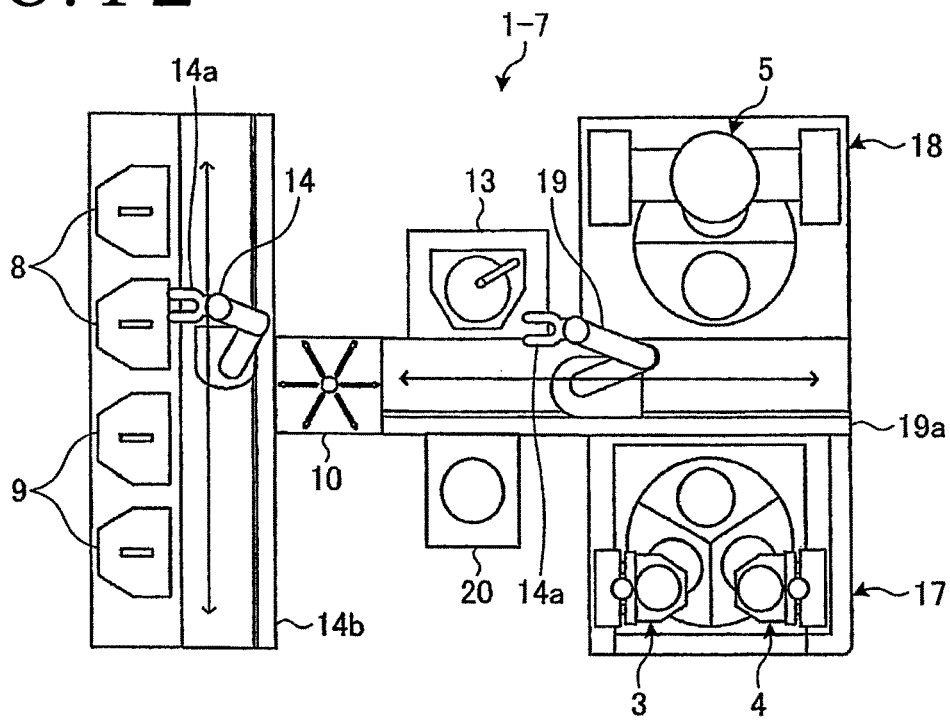
FIG. 12 is a plan view showing a processing system for performing a workpiece evaluating method according to a seventh preferred embodiment of the present invention.

An evaluating method according to a seventh preferred embodiment of the present invention will now be described with reference to the drawings. FIG. 12 is a plan view showing a processing system 1-7 for performing the workpiece evaluating method according to the seventh preferred embodiment. In FIG. 12, the same parts as those of the fifth preferred embodiment are denoted by the same reference symbols, and the description thereof will be omitted.

As shown in FIG. 12, the configuration of the processing system 1-7 according to the seventh preferred embodiment is the same as the configuration of the processing system 1-5 according to the fifth preferred embodiment except that the temporary setting portion 25 is omitted and the positioning means 10 is located at one end of the moving and supporting mechanism 19a and that the evaluating apparatus 20 is mounted at one end portion of the moving and supporting mechanism 19a to evaluate the gettering property after cleaning the device wafer W.

As similar to the first preferred embodiment, by operating the processing system 1-7, i.e., by performing the evaluating method according to the seventh preferred embodiment, the determination of whether or not the gettering property is good can be made without contaminating the device wafer W with metal elements. Further, as similar to the first preferred embodiment, the processing system 1-7 according to the seventh preferred embodiment employs so-called dry polishing for forming the gettering layer G having a gettering property. However, this preferred embodiment may adopt not only this dry polishing, but also any other processing methods capable of forming the gettering layer G having a gettering property. Examples of such a processing method include grinding using a high-mesh wheel, plasma etching after polishing the device wafer W, laser beam application, and ion beam application (see Japanese Patent Laid-open No. 2011-253983, for example). As similar to the first preferred embodiment, wet polishing may also be used.

Eighth Preferred Embodiment

Figure 13:
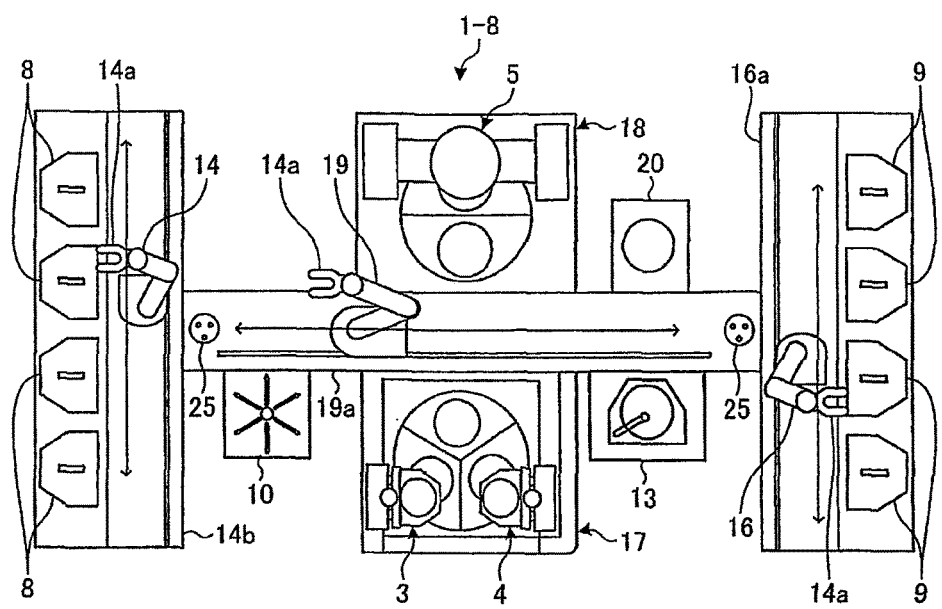
FIG. 13 is a plan view showing a processing system for performing a workpiece evaluating method according to an eighth preferred embodiment of the present invention.

An evaluating method according to an eighth preferred embodiment of the present invention will now be described with reference to the drawings. FIG. 13 is a plan view showing a processing system 1-8 for performing the workpiece evaluating method according to the eighth preferred embodiment. In FIG. 13, the same parts as those of the fifth preferred embodiment are denoted by the same reference symbols, and the description thereof will be omitted.

As shown in FIG. 13, the processing system 1-8 according to the eighth preferred embodiment includes a moving and supporting mechanism 14b for movably supporting first handling means 14 is mounted at one end of the moving and supporting mechanism 19a for movably supporting the transfer means 19. In addition, a moving and supporting mechanism 16a for movably supporting second handling means 16 is mounted at the other end of the moving and supporting mechanism 19a. Four cassettes 8 are arranged in a line adjacent to the moving and supporting mechanism 14b, and four cassettes 9 are arranged in a line adjacent to the moving and supporting mechanism 16a. The second handling means 16 is also configured by a robot pick including a U-shaped hand 14a similar to that of the first handling means 14. Further, another temporary setting portion 25 is provided at the other end portion of the moving and supporting mechanism 19a, wherein the device wafer W can be transferred to this temporary setting portion 25 by the transfer means 19 and can be next transferred to any one of the cassettes 9 by the second handling means 16. The moving direction of the second handling means 16 is parallel to the moving direction of the first handling means 14. Further, the cleaning means 13 is mounted at the other end portion of the moving and supporting mechanism 19a. The other configuration is the same as that of the fifth preferred embodiment shown in FIG. 10.

As similar to the first preferred embodiment, by operating the processing system 1-8, i.e., by performing the evaluating method according to the eighth preferred embodiment, the determination of whether or not the gettering property is good can be made without contaminating the device wafer W with metal elements. Further, as similar to the first preferred embodiment, the processing system 1-8 according to the eighth preferred embodiment employs so-called dry polishing for forming the gettering layer G having a gettering property. However, this preferred embodiment may adopt not only this dry polishing, but also any other processing methods capable of forming the gettering layer G having a gettering property. Examples of such a processing method include grinding using a high-mesh wheel, plasma etching after polishing the device wafer W, laser beam application, and ion beam application (see Japanese Patent Laid-open No. 2011-253983, for example). As similar to the first preferred embodiment, wet polishing may also be used.

Ninth Preferred Embodiment

Figure 14:
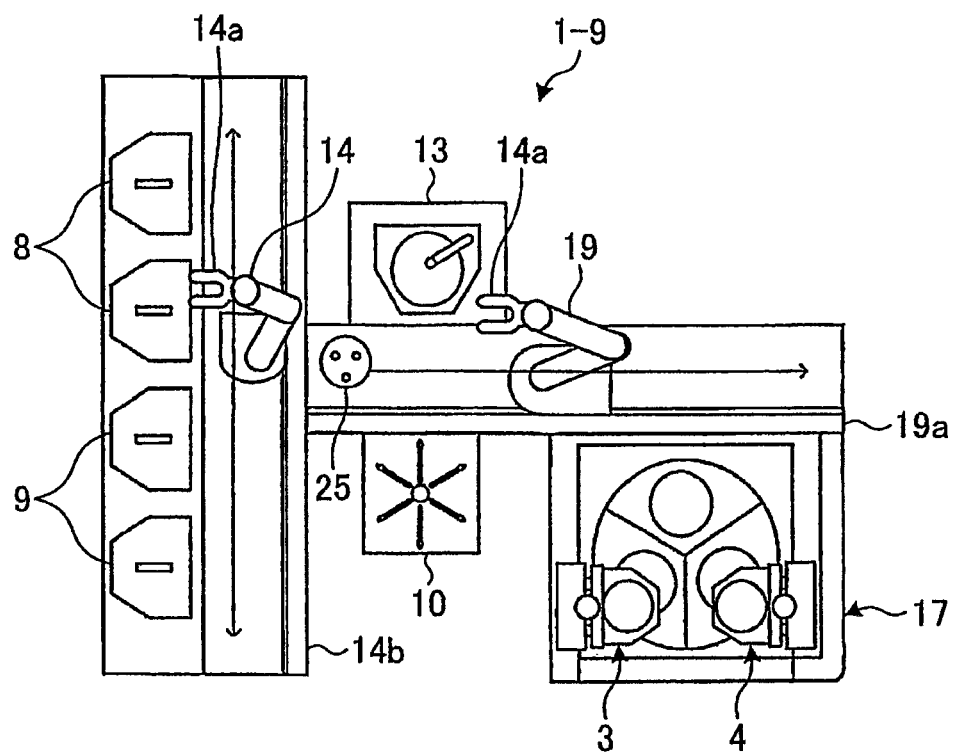
FIG. 14 is a plan view showing a processing system for performing a workpiece evaluating method according to a ninth preferred embodiment of the present invention.
Figure 14:
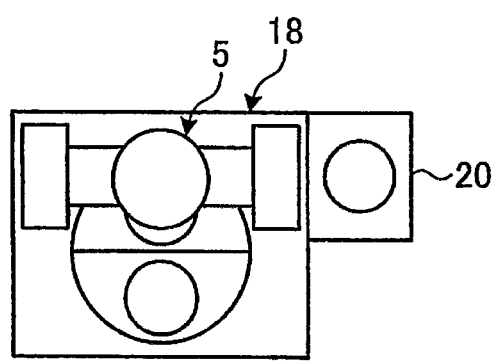

An evaluating method according to a ninth preferred embodiment of the present invention will now be described with reference to the drawings. FIG. 14 is a plan view showing a processing system 1-9 for performing the workpiece evaluating method according to the ninth preferred embodiment. In FIG. 14, the same parts as those of the fifth preferred embodiment are denoted by the same reference symbols, and the description thereof will be omitted.

As shown in FIG. 14, the configuration of the processing system 1-9 according to the ninth preferred embodiment is the same as the configuration of the processing system 1-5 according to the fifth preferred embodiment except that the polishing apparatus 18 and the evaluating apparatus 20 are separated from the moving and supporting mechanism 19a for movably supporting the transfer means 19 and that the processing system 1-9 further includes transfer means (not shown) for transferring the device wafer W from the grinding apparatus 17 to the polishing apparatus 18.

As similar to the first preferred embodiment, by operating the processing system 1-9, i.e., by performing the evaluating method according to the ninth preferred embodiment, the determination of whether or not the gettering property is good can be made without contaminating the device wafer W with metal elements. Further, as similar to the first preferred embodiment, the processing system 1-9 according to the ninth preferred embodiment employs so-called dry polishing for forming the gettering layer G having a gettering property. However, this preferred embodiment may adopt not only this dry polishing, but also any other processing methods capable of forming the gettering layer G having a gettering property. Examples of such a processing method include grinding using a high-mesh wheel (high-mesh abrasive grains), plasma etching after polishing the device wafer W, laser beam application, and ion beam application (see Japanese Patent Laid-open No. 2011-253983, for example). As similar to the first preferred embodiment, wet polishing may also be used.

In the processing systems 1 to 1-9 according to the first to ninth preferred embodiments mentioned above, the handling means 14 and the transfer means 19 are both robot picks each having the U-shaped hand 14a adapted to hold part of the device wafer W under suction. As a modification, the U-shaped hand 14a may be replaced by a suction pad adapted to hold the whole surface of the device wafer W under suction. Further, while the device wafer W is transferred between the handling means 14 and the transfer means 19 through the temporary setting portion 25 in the above preferred embodiments, the device wafer W may be directly transferred between the handling means 14 and the transfer means 19. Particularly in the case that the device wafer W to be transferred is thin, this transfer operation is effective. While the evaluating apparatus 20 constitutes each of the processing systems 1 to 1-9 according to the first to ninth preferred embodiments, the evaluating apparatus in the present invention may constitutes a device manufacturing system. That is, the evaluating method in the present invention may be included in a device manufacturing method. Further, the differential signal may not be used to evaluate the gettering property according to the intensity of the microwaves MR reflected from the light applied area R. Further, the gettering property may be evaluated according to a so-called recombination lifetime, or the duration from the time the application of the excitation light L is stopped to the time the intensity of the microwaves MR reflected from the light applied area R becomes l/e or less.

According to the first to ninth preferred embodiments, the following evaluating apparatus, processing system, and processing method may be obtained.

APPENDIX 1

An evaluating apparatus for evaluating the gettering property of a workpiece having a plurality of devices formed on the front side of the workpiece and having a gettering layer formed inside the workpiece, the evaluating apparatus including:

excitation light applying means for applying excitation light for exciting a carrier to the workpiece;

microwave applying means for applying microwaves to a light applied area where the excitation light is applied and also to an area other than the light applied area on the workpiece;

measuring means for measuring the intensity of microwaves reflected from the light applied area and from the area other than the light applied area and then subtracting the intensity of the microwaves reflected from the area other than the light applied area from the intensity of the microwaves reflected from the light applied area to thereby obtain a differential signal; and means for determining the gettering property of the gettering layer according to the intensity of the differential signal obtained by the measuring means.

APPENDIX 2

A processing system including:
an evaluating apparatus according to Appendix 1; and
processing means for processing the workpiece.

APPENDIX 3

A processing method for a workpiece having a plurality of devices formed on the front side of the workpiece and having a gettering layer formed inside the workpiece, the processing method including:

a first step of applying excitation light for exciting a carrier to the workpiece;

a second step of applying microwaves to a light applied area where the excitation light is applied and also to an area other than the light applied area on the workpiece;

a third step of measuring the intensity of microwaves reflected from the light applied area and from the area other than the light applied area and then subtracting the intensity of the microwaves reflected from the area other than the light applied area from the intensity of the microwaves reflected from the light applied area to thereby obtain a differential signal; and a fourth step of determining the gettering property of the gettering layer according to the intensity of the differential signal obtained in the third step.

The present invention is not limited to the above preferred embodiments and modifications, but various other modifications may be made without departing from the scope of the present invention.

The present invention is not limited to the details of the above described preferred embodiments. The scope of the invention is defined by the appended claims and all changes and modifications as fall within the equivalence of the scope of the claims are therefore to be embraced by the invention.

What is claimed is:

1. A workpiece evaluating method for evaluating the gettering property of a workpiece having a plurality of devices formed on a front side of said workpiece and having a gettering layer formed inside said workpiece, said workpiece evaluating method comprising:

an excitation light applying step of applying excitation light for exciting a carrier in said workpiece;

a microwave applying step of applying microwaves to a light applied area where said excitation light is applied and also to an area other than said light applied area on said workpiece, after performing said excitation light applying step;

a measuring step of measuring the intensity of said microwaves reflected from said light applied area and from the area other than said light applied area after performing said microwave applying step, and next subtracting the intensity of said microwaves reflected from the area other than said light applied area from the intensity of said microwaves reflected from said light applied area to thereby obtain a differential signal; and a gettering property determining step of determining the gettering property of said gettering layer according to the intensity of said differential signal obtained in said measuring step.

2. The workpiece evaluating method according to claim 1, wherein the frequency of said microwaves is 26 GHz.

3. The workpiece evaluating method according to claim 1, wherein the wavelength of said excitation light is 349 nm.

* * * * *